(12) United States Patent
Nitta et al.

(10) Patent No.: US 10,330,572 B2
(45) Date of Patent: Jun. 25, 2019

(54) SAMPLING LOCATION DISPLAYING APPARATUS AND SAMPLING METHOD

(71) Applicant: MITSUBISHI MATERIALS CORPORATION, Tokyo (JP)

(72) Inventors: Akira Nitta, Kagawa-gun (JP); Michiaki Onishi, Kagawa-gun (JP); Kenichi Tomioka, Kagawa-gun (JP); Tomohiro Tsutsui, Tokyo (JP); Makoto Takagi, Tokyo (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 176 days.

(21) Appl. No.: 15/119,243

(22) PCT Filed: Jun. 16, 2014

(86) PCT No.: PCT/JP2014/065867
§ 371 (c)(1),
(2) Date: Aug. 16, 2016

(87) PCT Pub. No.: WO2015/151301
PCT Pub. Date: Oct. 8, 2015

(65) Prior Publication Data
US 2017/0010190 A1  Jan. 12, 2017

(30) Foreign Application Priority Data

Mar. 31, 2014 (JP) .................. 2014-071988

(51) Int. Cl.
*H04N 7/18* (2006.01)
*G01N 1/28* (2006.01)
(Continued)

(52) U.S. Cl.
CPC ................ *G01N 1/28* (2013.01); *B09B 3/00* (2013.01); *B09B 5/00* (2013.01); *G01N 1/04* (2013.01);
(Continued)

(58) Field of Classification Search
USPC .............................................. 348/222.1, 95
See application file for complete search history.

(56) References Cited

U.S. PATENT DOCUMENTS 6,301,956 B1  10/2001  Fujita et al.
6,956,208 B2  10/2005  Reilly et al.
(Continued)

FOREIGN PATENT DOCUMENTS

CN         1661354 A     8/2005
CN       103234798 A     8/2013
(Continued)

OTHER PUBLICATIONS

Office Action dated Sep. 19, 2017, issued for the Japanese patent application No. 2014-071988 and English translation thereof.
(Continued)

*Primary Examiner* — Nigar Chowdhury
(74) *Attorney, Agent, or Firm* — Locke Lord LLP; James E. Armstrong, IV; Nicholas J. DiCeglie, Jr.

(57) ABSTRACT

According to the sampling method of the aspect of the present invention, the coordinate (location information) of the sampling location on the sampling specimen is generated randomly by the controller, such as a personal computer, of the sampling location display. Based on the location information, the sampling location is displayed on the sampling specimen, which is a part of the recycled raw material, by laser light. Because of this, arbitrariness, in which the operator artificially selects the sampling location, during incremental sampling for setting the average quality of the
(Continued)

sampling specimen, such as the average content of valuable metal, can be excluded reliably.

8 Claims, 7 Drawing Sheets

(51) Int. Cl.
    *G01N 1/04*     (2006.01)
    *B09B 3/00*     (2006.01)
    *B09B 5/00*     (2006.01)
    *G06T 1/00*     (2006.01)
    *H04N 9/31*     (2006.01)
    *H04N 5/228*     (2006.01)

(52) U.S. Cl.
    CPC ........... *G06T 1/0007* (2013.01); *H04N 7/183* (2013.01); *H04N 9/3161* (2013.01); *G01N 2001/282* (2013.01)

(56) References Cited

U.S. PATENT DOCUMENTS

| | | | |
|---|---|---|---|
| 2004/0043392 A1 | 3/2004 | Washiyama et al. | |
| 2004/0183006 A1* | 9/2004 | Reilly | H01J 49/0004 250/282 |
| 2005/0102056 A1* | 5/2005 | Du | B01L 9/50 700/214 |
| 2005/0259256 A1 | 11/2005 | Anselmetti et al. | |
| 2006/0171656 A1* | 8/2006 | Adachi | B23K 26/0066 385/147 |
| 2007/0099017 A1* | 5/2007 | Hayakawa | B32B 27/08 428/480 |
| 2008/0144009 A1* | 6/2008 | Krivacic | G01N 21/6428 356/73 |
| 2009/0057552 A1* | 3/2009 | Yamada | H01J 49/0418 250/288 |
| 2009/0286892 A1* | 11/2009 | Isozaki | B29B 17/02 521/40 |
| 2010/0157086 A1* | 6/2010 | Segale | G01N 21/6458 348/222.1 |
| 2010/0234550 A1* | 9/2010 | Hassan | B01F 7/00766 526/351 |
| 2010/0317761 A1* | 12/2010 | Nien | E06B 9/266 521/182 |
| 2011/0174191 A1* | 7/2011 | Umemura | C08L 33/02 106/164.4 |
| 2011/0299786 A1* | 12/2011 | Kazama | G06K 9/0063 382/225 |
| 2012/0193530 A1* | 8/2012 | Parker | G01N 21/6428 250/307 |
| 2012/0273421 A1* | 11/2012 | Perry | B01D 61/027 210/651 |
| 2013/0329233 A1* | 12/2013 | Cohen | G01B 9/04 356/624 |

FOREIGN PATENT DOCUMENTS

| | | |
|---|---|---|
| CN | 103245286 A | 8/2013 |
| CN | 203351550 U | 12/2013 |
| JP | 02-205745 A | 8/1990 |
| JP | 05-265637 A | 10/1993 |
| JP | 07-120264 A | 5/1995 |
| JP | 09-053918 A | 2/1997 |
| JP | 10-332588 A | 12/1998 |
| JP | 11-248415 A | 9/1999 |
| JP | 2000-155081 A | 6/2000 |
| JP | 2000-180330 A | 6/2000 |
| JP | 2001-218546 A | 8/2001 |
| JP | 2003-106962 A | 4/2003 |
| JP | 2003-284549 A | 10/2003 |
| JP | 2007-225285 A | 9/2007 |
| JP | 2010-223905 A | 10/2010 |
| JP | 2011-126677 A | 6/2011 |
| JP | 2011-252870 A | 12/2011 |
| WO | 99/065625 A1 | 12/1999 |
| WO | 2012/072468 A1 | 6/2012 |

OTHER PUBLICATIONS

Notice of Allowance dated Jan. 16, 2018, issued for the Japanese patent application No. 2014-071988 and English translation thereof.
Supplementary European Search Report dated Nov. 24, 2017, issued for the European patent application No. 14887947.1.
"Particulate materials—General rules for methods of sampling", Japanese Industrial Standard, JIS-M8100, 1992, pp. 1-28. (cited in ISR).
International Search Report dated Sep. 9, 2014, issued for PCT/JP2014/065867 and English translation thereof.
Office Action dated Feb. 5, 2018, issued for the Chinese patent application No. 201480066552.0 and English translation thereof.

* cited by examiner

SAMPLING LOCATION DISPLAYING APPARATUS AND SAMPLING METHOD

TECHNICAL FIELD

The present invention relates to a sampling location displaying apparatus that displays a sampling location on a sample during sampling from a specimen and a sampling method using the sampling apparatus.

Priority is claimed on Japanese Patent Application No. 2014-071988, filed on Mar. 31, 2014, the content of which is incorporated herein by reference.

BACKGROUND ART

Gold, silver, copper, palladium, and the like are included in electric boards, flexible substrates, IC chips, cellular phones, and the like. In addition, silver is included in photographic films, movie films, X-ray films, photographic papers, and the like.

Thus, recovery of the above-mentioned valuable metals is performed by using these electric boards, IC chips, cellular phones, flexible substrates, films, photographic papers, and the like as recycled raw materials in the copper refining process. For example, in the copper refining process, slug (molten body), combustion ash, or the like is obtained by feeding the recycled materials into a copper smelting furnace or by incinerating/melting them in a rotary kiln or the like. Then, the slug, combustion ash, or the like is fed into a copper smelting furnace or the like.

The transaction prices of the recycled raw materials, such as electric boards, IC chips, cellular phones, flexible substrates, film, photographic papers, and the like, are determined based on the content of the valuable metals included in the recycled raw materials.

For example, sampling apparatuses and sampling methods for automatically obtaining samples for evaluation from recycled raw materials are proposed in Patent Literatures 1 to 3 (PTLs 1 to 3).

However, there are various properties in wastes of electric boards, IC chips, cellular phones, flexible substrates, films, photographic papers, and the like, which are the recycled raw materials. Thus, occasionally, the sampling apparatuses disclosed in PTLs 1-3 cannot be used mainly due to limitation of their size surfaces. Because of this, sampling from the above-mentioned recycled raw materials has been performed manually in accordance with the procedure defined by JIS-M8100 (1992) (hereinafter, referred as "the JIS standard")

CITATION LIST

Patent Literature

PTL 1: Japanese Unexamined Patent Application, First Publication No. 2003-106962 (A)
PTL 2: Japanese Unexamined Patent Application, First Publication No. 2010-223905 (A)
PTL 3: Japanese Unexamined Patent Application, First Publication No. 2011-126677 (A)

SUMMARY OF INVENTION

Technical Problem

However, in the case where the operation for collecting samples for evaluation from recycled raw materials is performed manually by human, it may not be possible to evaluate the recycled raw material correctly, since a part, in which the valuable metals are concentrated; or a part not containing the valuable metal might be chosen and collected during collecting the evaluation samples. Therefore, there is a possibility that the discrepancy between the evaluation on the side delivering the recycled raw materials and the evaluation on the side receiving them occurs.

The present invention is made under the above-described circumstances. The purpose of the present invention is to provide a sampling location displaying apparatus and a sampling method enabling sampling without arbitrariness during sampling from specimen manually.

Solution to Problem

In order to solve the technical problem described above, a sampling location displaying apparatus that displays a sampling location on a sample, which is an aspect of the present invention, includes: a laser irradiation part that sends a laser light irradiation toward a sample spread on a sampling field and displays a sampling location mark in a predetermined shape on the sample; and a controller that controls the laser irradiation part.

According to the sampling apparatus of the aspect of the present invention, the sampling location is displayed on the sample by laser light. By using the sampling apparatus having this configuration, the sampling location being chosen with arbitrariness can be prevented even in the case where collection is performed manually during sampling from specimen. Therefore, an increment having a quality closer to the accurate average quality of the specimen can be sampled even if the specimen has a shape not suitable for auto sampling, for example.

In the aspect of the present invention described above, the controller may be configured to generate random location information on the sample and outputs the random location information to the laser irradiation part, and the laser irradiation part is configured to display the sampling location mark on a random location on the sample based on the random location information.

By displaying the sampling location mark on random locations on the specimen based on the random location information on the specimen, sampling can be performed randomly without arbitrariness. Because of this, an increment having a quality closer to the accurate average quality of the specimen can be sampled more reliably.

In the aspect of the present invention described above, the sampling location mark may be configured in such a way that each of a displayed shape; brightness; and color of the sampling location mark is modifiable arbitrarily.

Because of this, the sampling location mark that is highly visible and easily identifiable can be displayed in consideration of characteristics of the sampled specimen against light; and workability in sampling can be improved.

Other aspect of the present invention is a sampling method using the sampling location displaying apparatus according to the above-described aspect of the present invention, the sampling method including the steps of: raking a sample after spreading the sample in a sampling field; sending the laser light irradiation toward the raked sample from the sampling location displaying apparatus; and scooping up a part of the sample on a location where the sampling location mark is displayed by using a sampling tool.

In this sampling method, which is the other aspect of the present invention, the sampling location is displayed on the specimen by laser light by using the above-described sampling location displaying apparatus that is the aspect of the present invention. Because of this, sampling can be performed without arbitrariness during sampling from specimen even in the case where sampling is performed manually from a specimen not suitable for automatic sampling. Therefore, an increment having a quality closer to the accurate average quality of the specimen can be sampled.

Other aspect of the present invention is a sampling method using the sampling location displaying apparatus according to the above-described aspect of the present invention, the sampling method including the steps of: raking a sample after spreading the sample in a sampling field; sending the laser light irradiation toward the raked sample from the sampling location displaying apparatus; and scooping up a part of the sample on a location where the sampling location mark is displayed by using a sampling tool, wherein the sampling location mark indicates the sampling location randomly selected on the sample.

According to the sampling method, which is the above-described other aspect of the present invention, sampling can be performed randomly without arbitrariness by displaying the sampling location mark on random locations on the specimen. Therefore, an increment having a quality closer to the accurate average quality of the specimen can be sampled more reliably.

In the sampling methods of the above-described aspects of the present invention, the sample may include a recycled raw material having a longest side of 10 cm or more.

In the sampling methods configured as described above, sampling can be performed without arbitrariness even if it is sampling from the recycled raw material that has a relatively large size and is not suitable for auto sampling.

Advantageous Effects of Invention

According to aspects of the present invention, a sampling location displaying apparatus; and a sampling method, in which sampling can be performed without arbitrariness during sampling for evaluating the specimen, can be provided.

DESCRIPTION OF EMBODIMENTS

Figure 1:
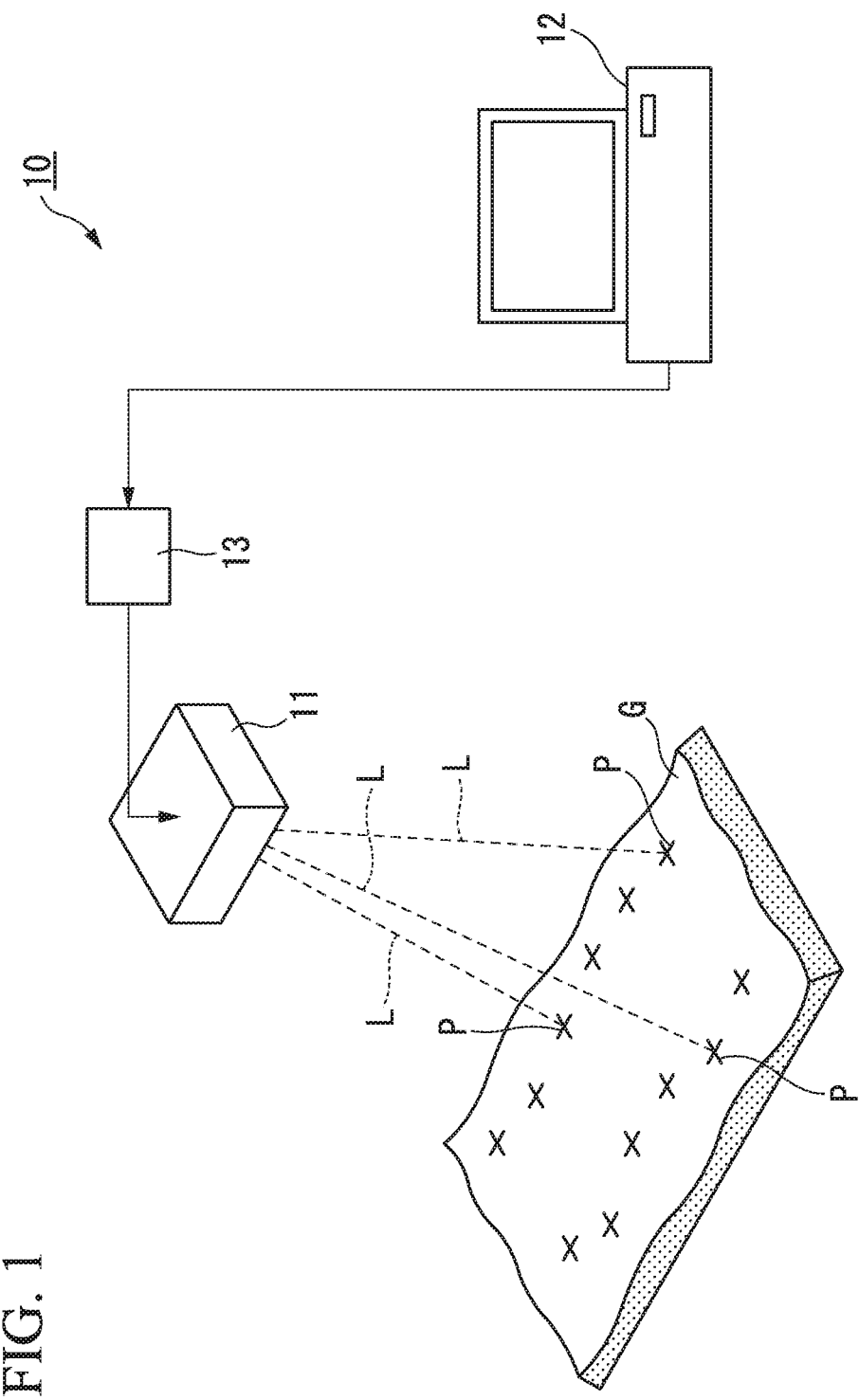
FIG. 1 is a diagram showing the sampling location displaying apparatus of the present invention.

The sampling location displaying apparatus and the sampling method of the present invention are explained in reference to drawings below. Each of embodiments described below is for specific explanation for the sake of better understanding of the technical concept of the present invention, and not for limiting the present invention unless otherwise stated. In addition, there are cases that an enlarged relevant part is shown for the sake of clarity of the characteristics of the present invention as a matter of convenience in the drawings used in the explanation below. Thus, sizes, ratio, and the like of each component may differ from the actual configurations.

[Sampling Location Displaying Apparatus]

The sampling location displaying apparatus of the present invention is explained.

FIG. 1 is a diagram showing the sampling location displaying apparatus of the present invention.

The sampling location displaying apparatus 10 includes: the laser irradiation part 11; the controller 12 configured to control the laser irradiation part 11; and the interface 13 connecting the laser irradiation part 11 and the controller 12.

The sampling location displaying apparatus 10 is provided to the sampling field where sampling of the sampling specimen G ("specimen" related to the present invention), which is a part of the recycled raw material corresponding to one lot. For example, the sampling specimen G is placed on an iron plate, which is laid on the sampling field, in such a way that the sampling specimen G is raked to be horizontally even as much as possible in accordance with the MS standard.

The laser irradiation part 11 is provided to the ceiling of the building accommodating the sampling field, for example; and is configured to be able to send laser light irradiation downward (floor direction)

The laser irradiation part 11 is constituted from a laser light source; a drive circuit driving the laser light source; and the like. As the laser light source, a diode pumped solid state layer is used, for example. As the laser light to irradiate, laser light L of visible light wavelength region, which is safe for the operator, is selected. For example, green laser light, wavelength of which is 532 nm, is selected. The output of the laser light L is set to about 30-50 mW, for example.

The laser light source configured as described above can send the laser light L irradiation to any location on the horizontally evenly raked sampling specimen G by a polygon mirror and/or a galvanometer mirror.

The controller 12 is constituted from a personal computer, for example. The controller 12 configured above outputs an irradiation signal to the laser irradiation part 11 in accordance with a program. The irradiation signal includes information such as the irradiation direction of the laser light L (coordinate data); the irradiation shape displayed by the laser light; and the like, for example.

The interface 13 connects the controller 12 and the laser irradiation part 11 electrically; and converts the irradiation signal output from the controller 12 to the control signal of the laser irradiation part 11.

The sampling location displaying apparatus 10 configured as described above operates in accordance with the operation program stored in the personal computer which is the controller 12. In the runtime of the operation program, the operator (hereinafter, "operator" correctively refers a person operating the sampling location displaying apparatus 10; a person raking the sampling specimen G; a person actually performing collection from the sampling specimen G by using the sampling tool; and the like) inputs the range information of the sampling specimen G spread in the sampling field; the display method; and the like by using a keyboard or the like.

The operation program is written in accordance with the JIS standard JIS-M8100 (1992) "Particulate material-General rules for methods of sampling" (hereinafter, referred as the JIS standard occasionally); the sampling condition individually determined between vendors; or the like. The JIS standard relates to: the chemical composition; moisture; granularity; physical characteristics; and the matters determining average values of these characteristics; and the collecting method of the specimen; the method of preparing testing samples; and the like are defined in the JIS standard. In addition, the sampling condition individually determined between vendors is the specific procedure for collecting specimen; the method of preparing testing samples; and the like, for example.

In addition to these, a procedure for collecting the specimen and/or the method of preparing the testing sample may be defined as needed and an operation program in accordance with the definitions may be used.

The controller 12 runs the operation program and generates the locations where the sampling location are displayed and the number of the locations for the laser irradiation part 11 based on the range information (information about approximate lengths in the X direction and the Y direction in the range where the sampling specimen G is spread in the sampling field) of the sampling specimen G, which is input in advance.

At this time, in sampling location generation, the operation program generates random numbers by the personal computer, which is the controller 12; and determines sampling location s randomly based on these random numbers. Generally, a computer can only generate definitive pseudorandom numbers obtained by calculation without an external input. Therefore, the random numbers in this context include the pseudorandom numbers. It is preferable that they are random numbers generated by a hardware for inputting external entropy. For example, the random numbers are generated by as CPU or a chipset with a built-in random number generator. Alternatively, they can be generated by utilizing the timing of input to the mouse or the timing of typing in the keyboard.

In addition, in generating the sampling locations, the operation program determines the sampling locations based on the method of determining sampling locations in accordance with the JIS standard.

The laser irradiation part 11 sends the laser light L irradiation toward the random locations on the sampling specimen G based on the location information of the random sampling locations obtained as explained above; and the laser irradiation part 11 displays (projects) the sampling location mark P, which instructs the sampling locations to the operator, on the sampling specimen G.

Figure 2A:
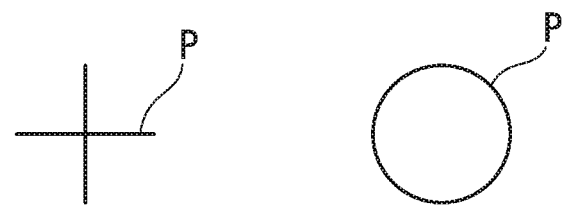
FIG. 2A is an explanatory diagram showing display examples of the sampling location mark.
Figure 2B:
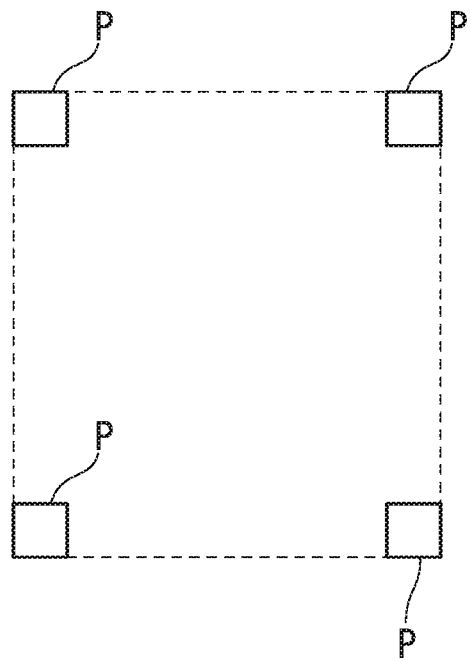
FIG. 2B is an explanatory diagram showing display examples of the sampling location mark.

The center of the he sampling location is shown by using the sampling location marks P of "○", "+", or the like as shown in FIG. 2A. Alternatively, four corners of a rectangle enclosing the sampling location are shown by the sampling location marks P of "□" as shown in FIG. 2B. These sampling location marks P can be shaped by scanning the laser light L.

According to the sampling location displaying apparatus 10 configured as described above, by determining the random display coordinates by using the random numbers, the controller 12 makes it possible to perform more reliably unbiased sampling of the sampling specimen G with no room for arbitrariness of the operator in determining the sampling location during determining the display coordinates of the sampling location marks P, which are displayed on the sampling specimen G.

To the above-described sampling location displaying apparatus 10, other function can be added further if need arises.

For example, it is preferable that a camera, which takes plan view images of the sampling specimen G viewed from above after raking the sampling specimen G by the operator, is provided to the laser irradiation part 11. It is preferable that the controller 12 performs mapping of the sampling specimen G based on the image information; and the sampling locations on the sampling specimen G are automatically and randomly set. This relieves the operator of the trouble doing measurement of the length of the sampling specimen G raked in the sampling field; inputting the measurement results to the controller 12; and the like.

In addition, it is preferable that the laser irradiation part is configured in such a way that color of the laser can be changed by modulating the wavelength range of the sending the laser light L irradiation. The selected wavelength can be output by changing temperature of the luminescent layer of the semiconductor laser element with current, a heater, or the like to change the refractive index of the semiconductor, for example.

Because of this, the operator can recognize the color of the sampling location mark P displayed on the sampling specimen G more easily from the overall color tone of the recycled raw material.

In addition, it is preferable that the laser irradiation part 11 is configured in such a way that the luminance of the sending the laser light L irradiation is variable.

By making the luminance of the sending the laser light L irradiation variable, for example, in the case where the sampling specimen G has a high overall content of highly reflective materials, the antiglare property can be improved by reducing the luminance of the sampling location mark P displayed on the sampling specimen G.

The displaying timing of the sampling location mark P can be set arbitrarily in the laser irradiation part 11. For example, the laser irradiation part 11 can be configured in such a way that the sampling location mark P in the subsequent random coordinate is displayed after input of sampling completion to the controller 12 by the operator. Alternatively, it can be configured in such a way that the sampling location mark P is displayed on the subsequent random coordinate automatically after the elapse of a predetermined time.

[Sampling Method]

The sampling method of the present invention using the sampling location displaying apparatus 10 configured as described above is explained in reference to FIG. 1, and FIGS. 3A-5.

Figure 3A:
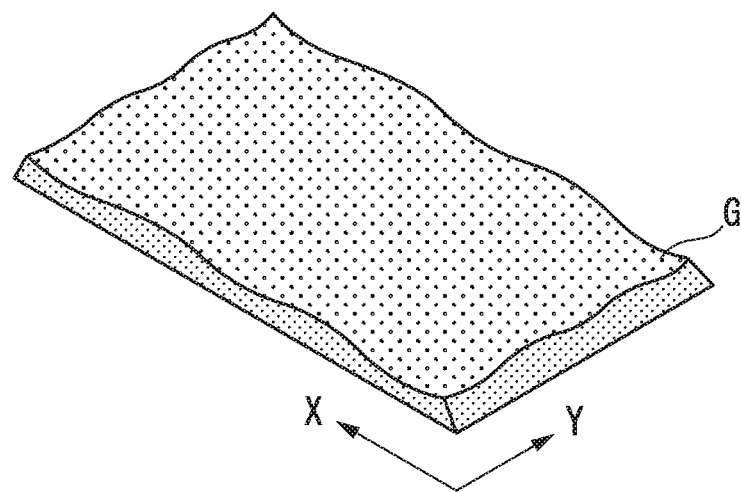
FIG. 3A is an explanatory diagram showing the sampling method of the present invention in a step-by-step manner.
Figure 3B:
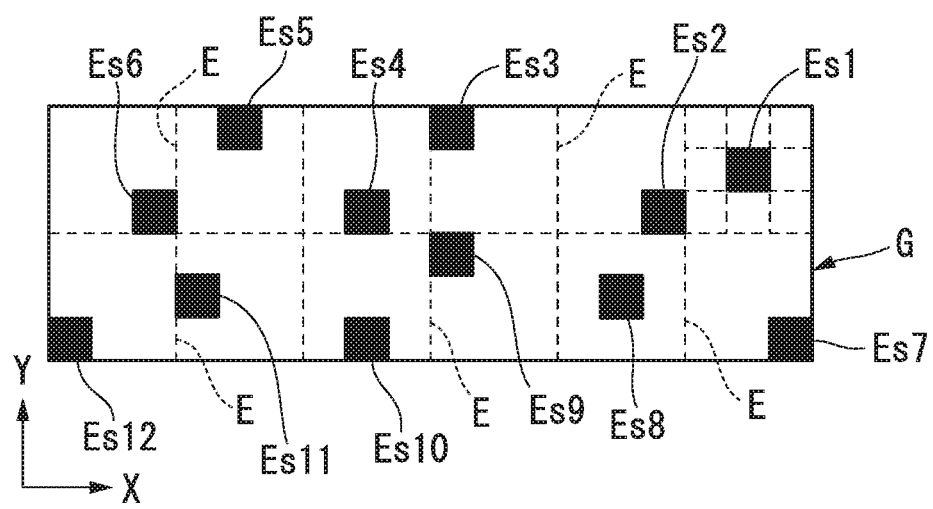
FIG. 3B is an explanatory diagram showing the sampling method of the present invention in a step-by-step manner.
Figure 3C:
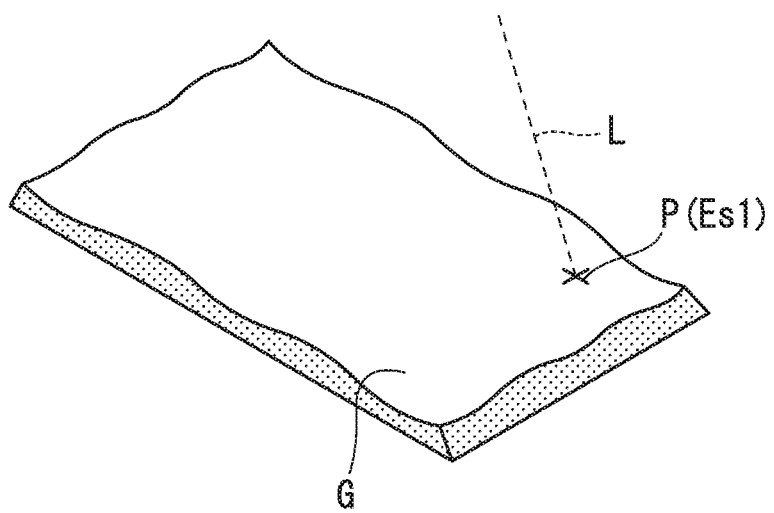
FIG. 3C is an explanatory diagram showing the sampling method of the present invention in a step-by-step manner.
Figure 4A:
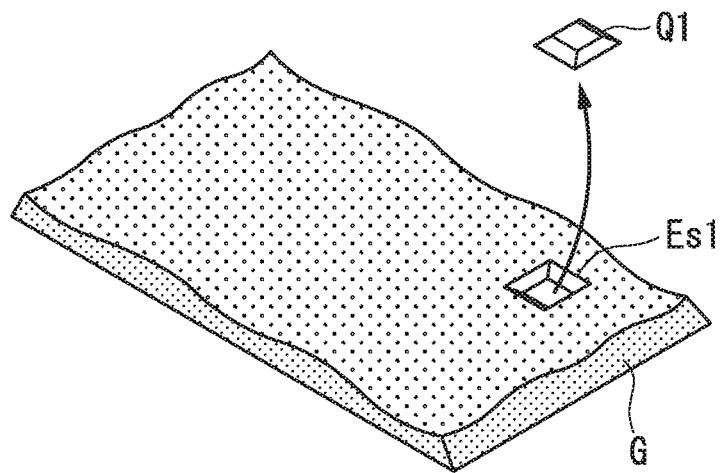
FIG. 4A is an explanatory diagram showing the sampling method of the present invention in a step-by-step manner.
Figure 4B:
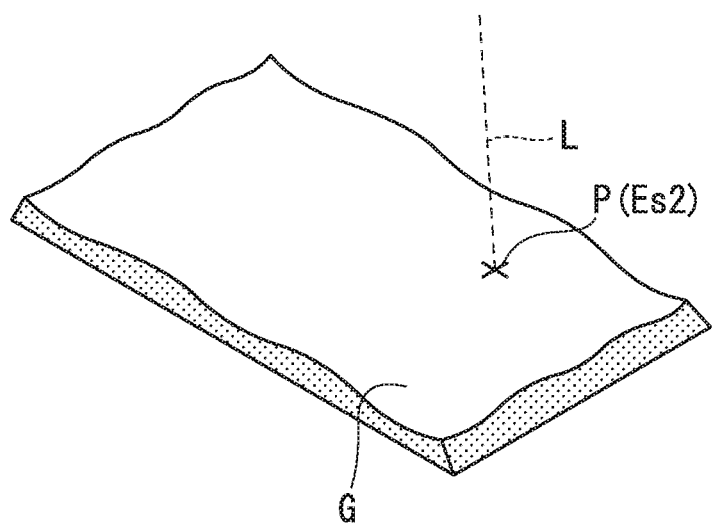
FIG. 4B is an explanatory diagram showing the sampling method of the present invention in a step-by-step manner.
Figure 4C:
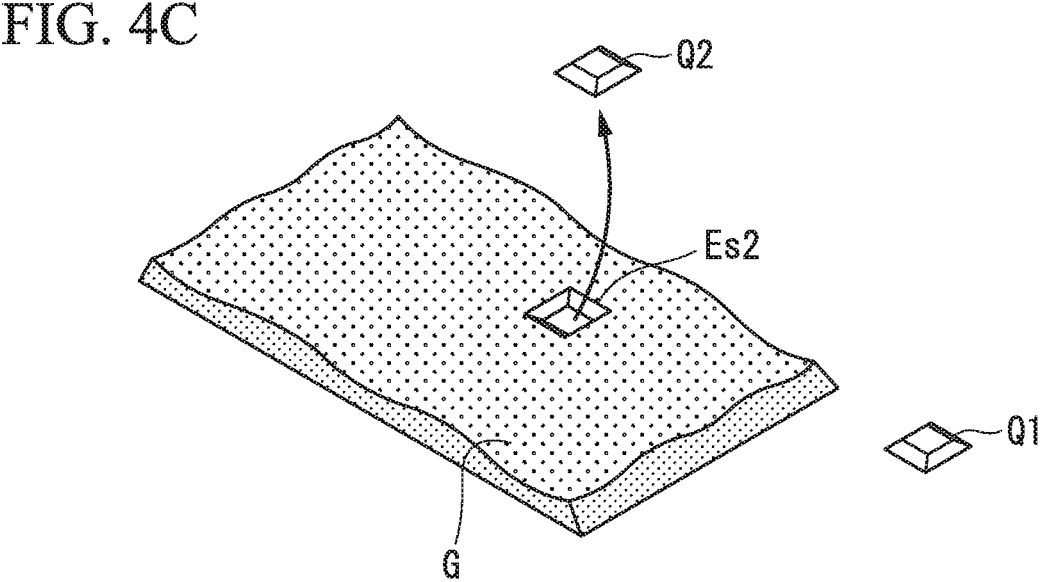
FIG. 4C is an explanatory diagram showing the sampling method of the present invention in a step-by-step manner.
Figure 5:
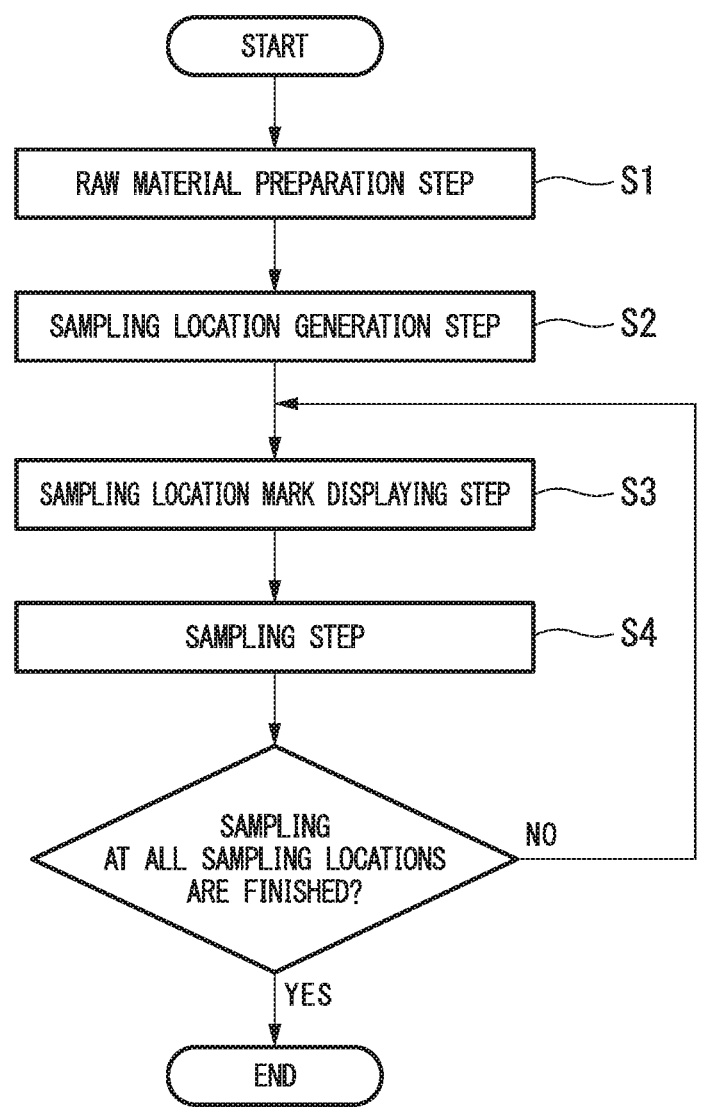
FIG. 5 is a flowchart showing the sampling method of the present invention in a step-by-step manner.

FIGS. 3A-3C; and FIGS. 4A-4C are explanatory diagrams showing the sampling method of the present invention in step-by-step manners. FIG. 5 is a flowchart showing the sampling method of the present invention in a step-by-step manner.

As the recycled raw material, which is an example of the specimen sampled by the sampling method of the present invention, ones that include a relatively large sized thing retaining the original form after crushing such as electric boards, flexible substrates, cellular phones, and the like, can be named. In that case, the length of the longest side of the relatively large sized thing is 10 cm or more. It is difficult to use the automatic sampling machine to the recycled raw material having such a relatively large size.

In the sampling method of the present invention, sampling from the sampling specimen ("specimen" related to the present invention) G, which is a part of the recycled raw material corresponding to one lot, is performed. In determining the average quality of the specimen, a part of the recycled material, which is made of a constant amount of the agglomerate mixture (lot) brought in a single round, is brought in to the sampling field, to which the sampling location displaying apparatus 10 is installed, as the sampling specimen G. Then, the sampling specimen G is spread on the iron plate as shown in FIG. 3A, for example. Then, the operator rakes the sampling specimen G with a tool or the like so that the sampling specimen G to have a constant height as much as possible (FIG. 5: Raw material preparation step S1).

Next, the operator measures lengths of the raked sampling specimen G in the X direction and the Y directions; and inputs the size, in which the sampling specimen G spreads, to the program for sampling (software) running in the controller 12 of the sampling location displaying apparatus 10.

The controller 12 lays out multiple rectangular regions E on the sampling specimen G as shown in FIG. 3B on the data, based on the input size, in which the sampling specimen G spreads. The number of the laid out rectangular regions is changed based on the input size in which the sampling specimen G spreads. The larger the size, the more of rectangular regions E laid out. Then, random numbers are generated to each of the rectangular regions E to generate the coordinates (location information) of the sampling locations randomly (FIG. 5: Sampling location generation step S2).

The rectangular regions E are laid out on the data of the sampling program for the sake of convenience in order to generate the coordinates (location information) of the sampling locations thoroughly all over the entire raked sampling specimen G. Thus, as an alternative way, a sampling program, which generates coordinates (location information) of the sampling locations randomly without setting these rectangular regions E, can be used. In this case, it is preferable that a program routine, which generates coordinates (location information) of the sampling locations thoroughly all over the entire sampling specimen G, is added in order to prevent locally biased coordinates (location information) of the sampling locations from being generated.

Specifically, the controller 12 lays out 12 rectangular regions E of 1.5 m square on the sampling specimen G, which is raked to be spread in such a way that it has the dimension of: 9 m in the X direction; 3 m in the Y direction; and 0.2 m of the height (thickness), on the data, for example, as shown in FIGS. 3A and 3B. Then, one of the sampling locations Es1 to Es12, each of which is 0.5 m square, is randomly chosen for each of the rectangular regions E.

In the example shown in FIG. 3B, nine sections are laid out in each of the rectangular regions E; and the sampling location in each of the rectangular regions E is determined by selecting one from the 9 sections randomly. Because of this, the randomly set total 12 locations are set among the sampling locations Es1 to Es12, each of which is 0.5 m square, on the sampling specimen G.

Instead of the method of selecting one section among multiple sections laid out in a single rectangular region E randomly, it can be done by following a procedure in which an arbitrary coordinate in a single rectangular region E is directly determined randomly. In this case, sampling from two different rectangular regions E at the same time is prevented by not selecting a coordinate in the vicinity of the boundary to the adjacent rectangular region.

Next, the controller 12 outputs the coordinate (location information) of the sampling location Es1 first among the coordinates (location information) of the randomly selected 12 sampling locations Es1 to Es12 to the laser irradiation part 11 through the interface 13.

The laser irradiation part 11 sends the laser light L irradiation toward the sampling location Es1 as shown in FIG. 3C based on the location information of the sampling location Es1, which is input from the controller 12. Then, the sampling location mark P is displayed (projected) on the randomly selected sampling location Es1 on the sampling specimen G (FIG. 5: Sampling location mark displaying step S3).

The sampling location mark P is displayed in the shape of "○", "+", or the like in the central coordinates of the sampling locations Es1 to Es12, each of which is 0.5 m square, for example. Alternatively, each of the four corners of the rectangle can be shown by "□" so as to enclose each region of the sampling locations Es1 to Es12. These sampling marks P can be continuously lighting-up or blinked. In the present embodiment, the sampling location mark P is shown by "+" on each of the central coordinates of the sampling location Es1 to Es12.

In displaying the sampling location mark P by sending the laser light irradiation L, by using green light laser in the visible light wavelength range as the laser source of the laser irradiation apparatus 11, the operation can be performed safely even if the operator does not wear the laser protection glasses or the like particularly.

Next, the operator collects the sampling specimen G on the sampling location Es1 on which the sampling location mark P is displayed as shown in FIG. 4A to obtain the sample (hereinafter referred as "increment") on each of the sampling locations (FIG. 5: Sampling step S4). In sampling, the operator scoops up the sampling specimen G corresponding to the part with the scoop for increment collection by using the scoop for increment collection described in the JIS standard, for example.

After completion of sampling of the increment Q1 on the sampling location Es1, the operator inputs completion of sampling on the sampling location Es1 to the controller 12. Then, the controller 12 outputs the coordinate (location information) of the randomly selected sampling location Es2 to the laser irradiation part 11 through the interface 13.

Instead of the method in which the operator inputs completion of sampling to the controller 12 every time after completion of sampling at one location, it can be configured in such a way that the process of completion of sampling is done by the controller 12 automatically after the elapse of a predetermined time.

The laser irradiation part 11 sends the laser light L irradiation toward the sampling location Es2 as shown in FIG. 4B based on the location information of the sampling location Es2 input from the controller 12. Then, the sampling location mark P is displayed (projected) on the randomly selected sampling location Es2 on the sampling specimen G (FIG. 5: Sampling location mark displaying step S3).

Then, the operator collects the increment Q2 on the sampling location Es2, on which the sampling location mark P is displayed, as shown in FIG. 4C (FIG. 5: Sampling step S4).

By repeating these steps, each of the increments Q1 to Q12 are obtained (sampling) from the sampling locations Es1 to Es12, which are randomly selected by the controller 12.

By following the above described steps, sampling of the increments from the recycled raw materials by the sampling method of the present invention is completed.

According to the sampling method of the present invention as described above, coordinates (location information) of the sampling locations of the recycled raw materials are generated randomly by the controller 12 of the sampling location displaying apparatus 10, such as a personal computer. Then, the sampling locations are displayed on the recycled raw materials by the laser light based on the location information. Because of this, the operator arbitrary selecting the sampling locations manually can be excluded reliably in sampling of the increments for determining the average quality of the recycled raw materials such as the average content amount of valuable metals.

After finely crushing the sampled increments Q1 to Q12, the average values of the chemical composition; moisture; granularity; physical characteristics; and other characteristics of the one lot of the recycled raw materials are determined by various methods of analysis.

Embodiments of the present invention are described above. However, the present invention is not particularly limited by the description, and it can be subjected to modifications as needed within range not diverting beyond the technical concept of the present invention.

For example, in the above-described embodiment, the example, in which the increments are sampled at the 12 locations for one lot of the recycled raw materials for sample extraction, is shown. However, the number of the increment sampling is set appropriately based on the amount of the recycled raw material. For example, the necessary minimum number of increments collected from a single lot is described in JIS-M8100 (1992). Thus, the number can be set complying with such a JIS standard.

In addition, in the above-described embodiment, the sampling location marks are displayed on the random locations within each of the rectangular regions by setting multiple rectangular regions on the data for the sake of convenience, in order to perform sampling thoroughly from the entire region, on which the sampling specimen G spreads. However, coordinates of the sampling locations can be generated randomly in such a way that the coordinates are dispersed over the entire region, on which the sapling specimen G spreads, evenly without setting these rectangular regions particularly instead. Alternatively, the sampling location marks may be displayed on constant locations set in advance on the sampling specimen G. Since qualities of the sampling specimen G existing on the constant locations set in advance differ in every lot of the sampling specimen G, sampling excluding the arbitrariness can be performed in this case too.

As the specimen preferably applied to the sampling location displaying apparatus and the sampling method of the present invention, in addition to the above-described recycled raw materials, materials taking time and effort for crushing for auto sampling, such as various ore, soil, lime, and the like, can be named.

EXAMPLE

Technical effects of the present invention were confirmed by performing the tests described below.

Examples of the Present Invention

In Examples of the present invention, the above-described sampling location displaying apparatus of the present invention was used. The random sampling locations were displayed on the recycled raw materials in accordance with the sampling method of the present invention. Then, increments were collected from these sampling locations by a less-experienced operator (years of experience: 0.5 year) on sampling.

The used recycled raw materials were: board scraps (5 Lots); copper containing gold and silver (2 Lots); and sludge (2 Lots). Twelve increments were collected and mixed into one portion later. As for the rest, details of sampling complied the JIS-M8100 (1992).

Comparative Example 1

In Comparative Example 1, an experienced operator having 15 years of experience on sampling collected increments from randomly selected sampling locations on the recycled raw materials. Used recycled raw materials and the number of the increments were the same as in Examples of the present invention. In addition, as for rest, details of sampling complied the JIS-M8100 (1992). The specimen was the recycled raw materials in two Flexible Container Bags, and they were spread on an iron plate with a height of 20 mm. The size of the spread specimen was about 4000 mm in the X direction and about 3000 mm in the Y direction.

Comparative Example 2

In Comparative Example 2, a less-experienced operator (years of experience: 0.5 year) on sampling performed sampling in the same condition as in Comparative Example 1 except for the operator.

Comparative Examples 3 and 4

In Comparative Examples 3 and 4, an experienced operator having 15 years of experience on sampling performed specimen collection arbitrary. In Comparative Example 3, the experienced operator performed specimen collection arbitrary to have a high quality. In Comparative Example 4, the experienced operator performed specimen collection arbitrary to have a low quality Then, testing samples of the sampled recycled raw materials were prepared. Then, the content amounts of the valuable metals (gold, silver, and copper) were analyzed and analysis results of Example of the present invention and Comparative Examples were compared. Gold and silver were analyzed by the dry assay method (complying with JIS-M8111); and copper was analyzed by the sodium thiosulfate titration method (complying with JIS-M8121) or the ICP emission spectrometry. Analysis results of gold, silver, and copper are shown in Tables 1, 2, and 3, respectively.

TABLE 1

| | Gold (Au) g/t | | | | |
|---|---|---|---|---|---|
| Raw materials | Example of the present invention | Comparative Example 1 | Comparative Example 2 | Comparative Example 3 | Comparative Example 4 |
| Board scrap A | 22.8 | 21.5 | 19.0 | 38.4 | 13.5 |
| Board scrap B | 10.9 | 11.7 | 9.6 | 23.1 | 9.6 |
| Board scrap C | 49.2 | 40.1 | 16.3 | 55.7 | 33.2 |
| Board scrap D | 16.3 | 23.2 | 13.3 | 17.2 | 17.2 |
| Board scrap E | 79.3 | 75.8 | 33.9 | 103.7 | 88.2 |

TABLE 1-continued

Gold (Au) g/t

| Raw materials | Example of the present invention | Comparative Example 1 | Comparative Example 2 | Comparative Example 3 | Comparative Example 4 |
|---|---|---|---|---|---|
| Copper containing gold and silver A | 236.1 | 262.9 | 164.4 | 403.2 | 166.8 |
| Copper containing gold and silver B | 144 | 168.3 | 72.7 | 117.4 | 132.3 |
| Sludge A | 541.1 | 466.2 | 460.0 | 693.3 | 226.8 |
| Sludge B | 358.9 | 382.6 | 447.3 | 639.9 | 317.7 |

TABLE 2

Silver (Ag) g/t

| Raw materials | Example of the present invention | Comparative Example 1 | Comparative Example 2 | Comparative Example 3 | Comparative Example 4 |
|---|---|---|---|---|---|
| Board scrap A | 498 | 463 | 165 | 564 | 336 |
| Board scrap B | 534 | 437 | 431 | 563 | 564 |
| Board scrap C | 778 | 825 | 333 | 1017 | 865 |
| Board scrap D | 588 | 532 | 410 | 1004 | 416 |
| Board scrap E | 2091 | 2476 | 1889 | 4435 | 1851 |
| Copper containing gold and silver A | 824 | 830 | 416 | 672 | 757 |
| Copper containing gold and silver B | 43 | 69 | 37 | 55 | 18 |
| Sludge A | 1385 | 1040 | 1726 | 2470 | 1226 |
| Sludge B | 23 | 23 | 19 | 39 | 14 |

TABLE 3

Copper (Cu) %

| Raw materials | Example of the present invention | Comparative Example 1 | Comparative Example 2 | Comparative Example 3 | Comparative Example 4 |
|---|---|---|---|---|---|
| Board scrap A | 11.78 | 11.99 | 8.20 | 20.11 | 8.32 |
| Board scrap B | 10.75 | 10.77 | 9.17 | 22.80 | 9.52 |
| Board scrap C | 15.55 | 15.43 | 7.86 | 12.68 | 14.28 |
| Board scrap D | 16.39 | 14.95 | 7.01 | 21.43 | 18.23 |
| Board scrap E | 1.26 | 1.48 | 1.07 | 1.61 | 0.53 |
| Copper containing gold and silver A | 23.47 | 25.56 | 29.25 | 28.48 | 20.78 |
| Copper containing gold and silver B | 36.11 | 33.23 | 30.13 | 40.74 | 21.38 |
| Sludge A | 17.18 | 18.46 | 5.68 | 19.46 | 11.58 |
| Sludge B | 21.49 | 23.22 | 17.59 | 27.09 | 22.71 |

Based on the results shown in Tables 1 to 3, arbitrariness was excluded in the content amount values in Example of the present invention, since they were intermediate values between the content amount values in Comparative Example 3, in which the experienced operator having 15 years of experience on sampling arbitrary performed sampling of parts including a higher amount of valuable metals; and the content amount values in Comparative Example 4, in which the experienced operator arbitrary performed sampling of parts including a lower amount of valuable metals. In addition, the content amount values in Example of the present invention were closely similar to the content amount values of the results in which the experience operator performed sampling in order to obtain the average quality as much as possible (Comparative Example 1). Thus, it is interpreted that the values are close the average quality of the entire recycled raw materials in Example of the present invention.

It is interpreted that the results in Comparative Example 1 are close to the average quality of the entire recycled raw materials. However, arbitrariness in sampling was not excluded completely in this case in the third party's view, since the operator directly involved in determining the sampling locations.

On the other hand, when the less-experienced operator (years of experience: 0.5 year) performed sampling in the condition identical to Comparative Example 1 (Comparative Example 2), large gaps of the values were observed relative to the results in which the veteran operator of 15 years of experience performed sampling in the condition (Comparative Example 1). In addition, when the less-experienced operator (years of experience: 0.5 year) performed specimen collection applying the present invention, results were nearly identical to the results by the experienced operator of 15 years of experience shown in Comparative Example 1 (Example of the present invention).

Based on the above-explained results, it was demonstrated that arbitrariness in sampling could be excluded completely; and sampling could be performed in such a way that the sampling had values closed to the average quality of the entire recycled raw materials, by applying the sampling location displaying apparatus of the present invention.

INDUSTRIAL APPLICABILITY

According to the sampling location displaying apparatus, which is an aspect of the present invention, the sampling location displaying apparatus and the sampling method, in which sampling can be performed excluding arbitrariness in sampling for evaluating specimen, can be provided. Therefore, the present invention has industrial applicability.

REFERENCE SIGNS LIST

10: Sampling location displaying apparatus
11: Laser irradiation part
12: Controller

What is claimed is:

1. A sampling location displaying apparatus configured to display a sampling location on a sample comprising:
    a laser irradiation part configured to send a laser light irradiation toward a sample spread on a sampling field and configured to display a sampling location mark in a predetermined shape on the sample; and
    a controller configured to control the laser irradiation part, wherein
    the sampling location mark is configured in such a way that each of a displayed shape, brightness, and color of the sampling location mark is modifiable arbitrarily;
    the sampling location is enclosed by the sampling location mark having a color different from an overall color tone of the sample;
    the controller is configured to generate random location information on the sample and configured to output the random location information to the laser irradiation part; and
    the laser irradiation part is configured to display the sampling location mark on a random location on the sample based on the random location information.

2. A sampling method using the sampling location displaying apparatus according to claim 1, the sampling method comprising the steps of:
    raking a sample after spreading the sample in a sampling field;
    sending the laser light irradiation toward the raked sample from the sampling location displaying apparatus; and
    scooping up a part of the sample on a location where configured to display to enclose the sampling location with a color tone different from the overall color tone of the sample is displayed by using a sampling tool.

3. The sampling method according to claim 2, wherein the sampling location mark indicates the sampling location randomly selected on the sample.

4. The sampling method according to claim 2, wherein the sample includes a recycled raw material having a longest side of 10 cm or more.

5. The sampling method according to claim 3, wherein the sample includes a recycled raw material having a longest side of 10 cm or more.

6. A sampling location displaying apparatus configured to display a sampling location on a sample comprising:
    a laser irradiation part configured to send a laser light irradiation toward a sample spread on a sampling field and configured to display a sampling location mark in a predetermined shape on the sample; and
    a controller configured to control the laser irradiation part, wherein
    the sampling location mark is configured in such a way that each of a displayed shape, brightness, and color of the sampling location mark is modifiable arbitrarily; and the sampling location is enclosed by the sampling location mark having a color different from an overall color tone of the sample,
    the controller is configured to generate random location information on the sample and to output the random location information to the laser irradiation part,
    the laser irradiation part is configured to display the sampling location mark on a random location on the sample based on the random location information, and
    the sampling location mark indicates the sampling location randomly selected on the sample.

7. A sampling method using the sampling location displaying apparatus according to claim 6, the sampling method comprising the steps of:
    raking a sample after spreading the sample in a sampling field;
    sending the laser light irradiation toward the raked sample from the sampling location displaying apparatus; and
    scooping up a part of the sample on a location where configured to display to enclose the sampling location with a color tone different from the overall color tone of the sample is displayed by using a sampling tool.

8. The sampling method according to claim 7, wherein the sample includes a recycled raw material having a longest side of 10 cm or more.

* * * * *